US008725264B2

(12) United States Patent
Soler Fernandez et al.

(10) Patent No.: US 8,725,264 B2
(45) Date of Patent: May 13, 2014

(54) METHOD FOR TREATING NEUROPATHIC PAIN

(75) Inventors: Maria Dolors Soler Fernandez, Badalona (ES); Hatice Kumru Kan, Badalona (ES); Raul Pelayo Vergara, Badalona (ES); Joan Vidal Samso, Badalona (ES); Jose Maria Tormos Munoz, Badalona (ES); Felipe Fregni, Badalona (ES); Xavier Navarro Acebes, Badalona (ES); Alvaro Pascual-Leone Garcia, Badalona (ES); Eloy Opisso Salleras, Badalona (ES)

(73) Assignee: Fundacio Privada Institut de Neurorehabilitacio Guttmann, Badalona (Barcelona) (ES)

( * ) Notice: Subject to any disclaimer, the term of this patent is extended or adjusted under 35 U.S.C. 154(b) by 0 days.

(21) Appl. No.: 13/197,883

(22) Filed: Aug. 4, 2011

(65) Prior Publication Data
US 2013/0035734 A1 Feb. 7, 2013

(51) Int. Cl.
*A61N 1/36* (2006.01)
(52) U.S. Cl.
USPC .......................................................... 607/45
(58) Field of Classification Search
USPC ................................................ 607/2–3, 45–46
See application file for complete search history.

(56) References Cited

U.S. PATENT DOCUMENTS

2010/0268287 A1* 10/2010 Celnik ............................... 607/2
2011/0065505 A1* 3/2011 Solanki et al. .................. 463/31

OTHER PUBLICATIONS

Alkadhi H, Brugger P, Boendermaker SH, Crelier G, Curt A, Hepp-Reymond MC, et al. What disconnection tells about motor imagery: evidence from paraplegic patients. Cereb Cortex 2005; 15: 131-40.
Andre-Obadia N, Mertens P, Gueguen R, Peyron R, Garcia-Larrea L. Pain relief by rTMS: Differential effect of current low but no specific action on pain subtypes. Neurology 2008; 71: 833-40.
Attal N, Fermanian C, Fermanian J, Lanteri-Minet M, Alchaar H, Bouhassira D. Neuropathic pain: are there distinct subtypes depending on the aetiology or anatomical lesion? Pain 2008; 138: 343-53.
Beck AT, Steer R, editors. An Inventory for Measuring Depression, TX: Psychological Corporation; 1996, 53-63.
Bouhassira D, Attal N, Fermanian J, Alchaar H, Gautron M, Masquelier E, et al. Development and validation of the neuropathic pain symptom inventory. Pain 2004; 108: 248-57.
Bryce TN, Budh CN, Cardenas DD, Dijkers M, Felix ER, Finnerup NB, et al. Pain after spinal cord injury: an evidence-based review for clinical practice and research. Report of the National Institute on Disability and Rehabilitation Research Spinal Cord Injury Measures meeting. J Spinal Cord Med 2007; 30: 421-40.
Cleeland CS, Ryan KM. Pain assessment: global use of the Brief Pain Inventory. Ann Acad Med Singapore 1994; 23: 129-38.
Costigan M, Scholz J, Woolf CJ. Neuropathic pain: a maladaptive response of the nervous system to damage. Annu Rev Neurosci 2009; 32: 1-32.

(Continued)

*Primary Examiner* — Amanda Patton
(74) *Attorney, Agent, or Firm* — RatnerPrestia (57) ABSTRACT

Provided is a method for treating neuropathic pain, including: providing, to a patient suffering from said neuropathic pain, a visual illusion to correct a mismatch between motor commands and sensory feedback; and applying a cranial stimulation to said patient during at least part of the duration of said visual illusion. This is particularly applicable to the treating of neuropathic pain in patients suffering from spinal cord injuries.

11 Claims, 3 Drawing Sheets

(56) References Cited

OTHER PUBLICATIONS

Chan BL, Witt R, Charrow AP, Magee A, Howard R, Pasquina PF, et al. Mirror Therapy for phantom limb pain. N. Engl J Med 2007; 357: 2206-7.
Cramer SC, Lastra L, Lacourse MG, Cohen MJ. Brain motor system function after chronic, complete spinal cord injury. Brain 2005; 128: 2941-50.
Cruccu G, Truini A. Sensory profiles: a new strategy for selecting patients in treatment trials for neuropathic pain. Pain 2009; 146: 5-6.
Dworkin RH, Turk DC, Farrar JT, Haythornthwaite JA, Jensen MP, Katz NP, et al. IMMPACT. Core outcome measures for chronic pain clinical trials: IMMPACT recommendations. Pain 2005; 113: 9-19.
Dworkin RH, Turk DC, Wyrwich KW, Beaton D, Cleeland CS, Farrar JT, et al. Interpreting the clinical importance of treatment outcomes in chronic pain clinical trials: IMMPACT recommendations. J Pain 2008; 9: 105-21.
Enzinger C, Ropele S, Fazekas F, Loitfelder M, Gorani F, Seifert T, et al. Brain motor system function in a patient with complete spinal cord injury following extensive brain-computer interface training. Exp Brain Res 2008; 190: 215-23.
Farrar JT, Young JP Jr, LaMoreaux L, Werth JL, Poole RM. Clinical importance of changes in chronic pain intensity measured on an 11-point numerical pain rating scale. Pain 2001; 94: 149-58.
Filimon F, Nelson JD, Hagler DJ, Sereno MI. Human cortical representations for reaching: mirror neurons for execution, observation, and imagery. Neuroimage 2007; 37: 1315-28.
Finnerup NB, Otto M, McQuay HJ, Jensen TS, Sindrup SH. Algorithm for neuropathic pain treatment: an evidence based proposal. Pain 2005; 118: 289-305.
Finnerup NB, Sørensen L, Biering-Sørensen F, Johannesen IL, Jensen TS. Segmental hypersensitivity and spinothalamic function in spinal cord injury pain. Exp Neurol 2007; 207: 139-49.
Fregni F, Boggio PS, Lima MC, Ferreira MJ, Wagner T, Rigonatti SP, et al. A sham-controlled, phase II trial of transcranial direct current stimulation for the treatment of central pain in traumatic spinal cord injury. Pain 2006; 122: 197-209.
Funase K, Tabira T, Higashi T, Liang N, Kasai T. Increased corticospinal excitability during direct observation of self-movement and indirect observation with a mirror box. Neurosci Lett 2007; 419: 108-12.
Gandiga PC, Hummel FC, Cohen LG. Transcranial DC stimulation (tDCS): a tool for double-blind sham-controlled clinical studies in brain stimulation. Clin Neurophysiol 2006; 117: 845-50.
Gangitano M, Mottaghy FM, Pascual-Leone A. Phase-specific modulation of cortical motor output during movement observation. Neuroreport 2001; 12: 1489-92.
Garcia-Larrea L, Peyron R, Mertens P, Gregoire MC, Lavenne F, Le Bars D, et al. Electrical stimulation of motor cortex for pain control: a combined PET-scan and electrophysiological study. Pain 1999; 83: 259-73.
Garry MI, Loftus A, Summers JJ. Mirror, mirror on the wall: viewing a mirror reflection of unilateral hand movements facilitates ipsilateral M1 excitability. Exp Brain Res 2005; 163: 118-22.
Giraux P, Sirigu A. Illusory movements of the paralyzed limb restore motor cortex activity. Neuroimage 2003; 20: 107-11.
Gustin SM, Wrigley PJ, Gandevia SC, Middleton JW, Henderson LA, Siddall PJ. Movement imagery increases pain in people with neuropathic pain following complete thoracic spinal cord injury. Pain 2008; 137: 237-44.
Hains BC, Saab CY, Waxman SG. Changes in electrophysiological properties and sodium channel Na(v)1.3 expression in thalamic neurons after spinal cord injury. Brain 2005; 128: 2359-71.
Harris JA. Cortical origin of pathological pain. Lancet 1999; 354: 1464-66.
Hotz-Boendermaker S, Funk M, Summers P, Brugger P, Hepp-Reymond MC, Curt A, et al. Preservation of motor programs in paraplegics as demonstrated by attempted and imagined foot movements. Neuroimage 2008; 39: 383-94.
Knerlich-Lukoschus F, Juraschek M, Blomer U, Lucius R, Mehdorn HM, Held-Feindt J. Force-dependent development of neuropathic central pain and time-related CCL2/CCR2 expression after graded spinal cord contusion injuries of the rat. J Neurotrauma 2008; 25: 427-48.
Kokotilo K, Eng J, Curt A. Reorganization and preservation of motor control of the brain in spinal cord injury: a systematic review. J Neurotrauma 2009; 26: 2113-26.
Kumru H, Soto O, Casanova J, Valls-Sole J. Motor cortex excitability changes during imagery of simple reaction time. Exp Brain Res 2008; 189: 373-8.
Lang N, Siebner HR, Ward NS, Lee L, Nitsche MA, Paulus W, et al. How does transcranial DC stimulation of the primary motor cortex alter regional neuronal activity in the human brain? Eur J Neurosci 2005; 22: 495-504.
Lefaucheur JP. Transcranial magnetic stimulation in the management of pain. Suppl Clin Neurophysiol 2004; 57: 737-48.
Lefaucheur JP, Drouot X, Menard-Lefaucheur I, Zerah F, Bendib B, Cesaro B, et al. Neurogenic pain relief by repetitive transcranial magnetic cortical stimulation depends on the origin and the site of pain. J Neurol Neurosurg Psychiatry 2004; 75: 612-16.
Lotze M, Flor H, Grodd W, Larbig W, Birbaumer N. Phantom movements and pain. An fMRI study in upper limb amputees. Brain 2001; 124: 2268-77.
Lotze M, Laubis-Herrmann U, Topka H. Combination of TMS and fMRI reveals a specific pattern of reorganisation in M1 in patients after complete spinal cord injury. Restorative Neurol Neurosci 2006; 24: 97-107.
MacIver K, Lloyd DM, Kelly S, Roberts N, Nurmikko T. Phantom limb pain, cortical reorganization and the therapeutic effect of mental imagery. Brain 2008; 131: 2181-91.
Maeda F, Kleiner-Fisman G, Pascual-Leone A. Motor facilitation while observing hand actions: specificity of the effect and role of observer's orientation. J Neurophysiol 2002; 87: 1329-35.
Marino RJ, Barros T, Biering-Sorensen F, Burns SP, Donovan WH, Graves DE, et al. 2002 ANSC. International standards for neurological classification of spinal cord injury. J Spinal Cord Med 2003; 26: 50-6.
Moore CI, Stern CE, Dunbar C, Kostyk SK, Gehi A, Corkin S. Referred phantom sensations and cortical reorganization after spinal cord injury in humans. Proc Natl Acad Sci USA 2000; 97: 14703-8.
Moseley GL. Using visual illusion to reduce at-level neuropathic pain in paraplegia. Pain 2007; 130: 294-8.
Nitsche MA, Liebetanz D, Antal A, Lang N, Tergau F, Paulus W. Modulation of cortical excitability by weak direct current stimulation-technical, safety and functional aspects. Suppl Clin Neurophysiol 2003; 56: 255-76.
Nitsche MA, Paulus W. Sustained excitability elevations induced by transcranial DC motor cortex stimulation in humans. Neurology 2001; 57: 1899-1901.
Nitsche MA, Seeber A, Frommann K, Klein CC, Rochford C, Nitsche MS, et al. Modulating parameters of excitability during and after transcranial direct current stimulation of the human motor cortex. J Physiol 2005; 568: 291-303.
Pascual-Leone A, Amedi A, Fregni F, Merabet LB. The plastic human cortex. Annu Rev Neurosci 2005; 28: 377-401.
Pascual-Leone A, Grafman J, Hallett M. Modulation of cortical motor output maps during development of implicit and explicit knowledge. Science 1994; 263: 1287-9.
Peyron R, Garcia-Larrea L, Deiber MP, Cinotti L, Conyers P, Sindou M, et al. Electrical stimulation of precentral cortical area in the treatment of central pain: electrophysiological and PET study. Pain 1995; 62: 275-86.
Ramachandram VS, Hirstein W. The perception of phantom limbs. The D.O. Hebb lecture. Brain 1998; 121: 1603-30.
Ramachandram VS, Rogers-Ramachandran D. Synaesthesia in phantom limbs induced with mirrors. Proc Biol Sci 1996; 263: 377-86.
Redondo E, Asensio E, Navarro X, Verdú E. Thermal and mechanical algesimetry and electrophysiological wind-up after graded spinal cord injury in the rat: relationship to astroglial and microglial reactivity. Glia 2009; 57: 5161. Abstract.

(56) References Cited

OTHER PUBLICATIONS

Sakamoto M, Muraoka T, Mizuguchi N, Kanosue K. Combining observation and imagery of an action enhances human corticospinal excitability. Neurosci Res 2009; 65: 23-7.

Siddall PJ, McClelland JM, Rutkowski SB, Cousins MJ. A longitudinal study of the prevalence and characteristics of pain in the first 5 years following spinal cord injury. Pain 2003; 103: 249-57.

Soler MD, Kumru H, Vidal J, Pelayo R, Tormos JM, Fregni F, et al. Referred sensations and neuropathic pain following spinal cord injury. Pain 2010. Advance Access published on May 12, 2010; doi:10.1016/j.pain.2010.04.027,192-98.

Soler MD, Sauri-Ruiz J, Curcoll ML, Benito-Penalva J, Opiso-Salleras E, Vidal-Samsó J. Characteristics of chronic neuropathic pain and their relationship with psychological well-being in spinal cord injury patients. Rev Neurol 2007; 44: 3-9. (Spanish with English Abstract).

Stinear CM, Byblow WD. Modulation of corticospinal excitability and intracortical inhibition during motor imagery is task-dependent. Exp Brain Res 2004; 157: 351-8.

Strafella AP, Vanderwerf Y, Sadikot AF. Transcranial magnetic stimulation of the human motor cortex influences the neuronal activity of subthalamic nucleus. Eur J Neurosci 2004; 20: 2245-9.

Wagner T, Valero-Cabre A, Pascual-Leone A. Noninvasive human brain stimulation. Annu Rev Biomed Eng 2007; 9: 527-65.

Waxman SG, Hains BC. Fire and phantoms after spinal cord injury: Na+ channels and central pain. Trends Neurosci 2006; 29: 207-15.

Widerström-Noga EG Turk DC. Types and effectiveness of treatments used by people with chronic pain associated with spinal cord injuries: influence of pain and psychosocial characteristics. Spinal Cord 2003; 41: 600-9.

Woolf CJ. Dissecting out mechanisms responsible for peripheral neuropathic pain: implications for diagnosis and therapy. Life Sci 2004; 74: 2605-10.

Wrigley PJ, Press SR, Gustin SM, Macefield VG, Gandevia SC, Cousins MJ, et al. Neuropathic pain and primary somatosensory cortex reorganization following spinal cord injury. Pain 2009; 141: 52-9.

Yezierski RP. Spinal cord injury: a model of central neuropathic pain. Neurosignals 2005; 14: 182-93.

Yoon YW, Dong H, Arends JJ, Jacquin MF. Mechanical and cold allodynia in a rat spinal cord contusion model. Somatosens Mot Res 2004; 21: 25-31.

Pascual-Leone et al., "Study and Modulation of Human Cortical Excitability With Transcranial Magnetic Stimulation," J Clin Neurophyscol vol. 15, No. 4, Jul. 1998, pp. 333-343.

Hardwick et al., "A quantitative meta-analysis and review of motor learning in the human brain," NeuroImage 67 (2013) pp. 283-297.

Ramachandran et al., "The use of visual feedback, in particular mirror visual feedback, in restoring brain function," Brain 2009: 132; pp. 1693-1710.

Pascual-Leone et al., "Reorganization of human cortical motor output maps following traumatic forearm amputation," NeuroReport 7 (1996), pp. 2068-2070.

Ramachandran et al., "Touching the phantom limb," Nature, vol. 377, Oct. 12, 1995, pp. 489-490.

Pascual-Leone et al., "The metamodal organization of the brain," Progress in Brain Research, vol. 134, 2001, pp. 1-19.

\* cited by examiner

METHOD FOR TREATING NEUROPATHIC PAIN

FIELD OF THE ART

The present invention generally relates to a method for treating neuropathic pain, comprising providing, to a patient suffering from said neuropathic pain, a visual illusion to correct a mismatch between motor commands and sensory feedback, and more particularly to a method further comprising applying a cranial stimulation to said patient during at least part of the duration of said visual illusion.

The method of the invention is particularly applicable to patients suffering from spinal cord injuries.

PRIOR STATE OF THE ART

Neuropathic pain affects ~40% of patients following spinal cord injury (SCI) (Siddall et al., 2003; Widerström-Noga and Turk, 2003; Soler et al., 2007) and represents a highly disabling clinical condition. The injured spinal somatosensory circuitry is thought to generate aberrant nociceptive impulses that are interpreted by the brain as pain (Yezierski, 2005). Thalamic integrative circuits may also act as generators and amplifiers of nociceptive signals (Hains et al., 2005, Waxman and Haines, 2006). Sensory deafferentation after SCI induces profound and long-lasting reorganization of the cortical and subcortical sensory maps in the adult brain (Lotze et al., 2006; Kokotilo et al., 2009; Wrigley et al., 2009). Pathophysiological consequences of such cortical plasticity may underlie the development of phantom sensations and pain (Moore et al., 2000; Lotze et al., 2001; Wrigley et al., 2009; Soler et al., 2010). Strategies aimed at reversing or modulating the somatosensory neural reorganization after injury may be valuable alternative therapeutic approaches to neuropathic pain.

Examples of such approaches that have shown some promise for the treatment of neuropathic pain following SCI or limb amputation include the use of movement imagery (Gustin et al., 2008; MacIver et al., 2008), mirror therapy (Ramachandran and Hirstein, 1998; Giraux and Sirigu, 2003; Chan et al., 2007) or 'virtual' mirror therapy (Moseley, 2007). Long-term pain relief was achieved by repeated treatment sessions in which patients were given the visual illusion that they could move and use again their deafferented or missing limbs. Pain relief presumably involves correction of the incongruence between motor output and sensory feedback, and normalization of cortical somatosensory representation maps, induced by the visual input of movements of the paralysed/missing limbs (Ramachandran and Rogers-Ramachandran, 1996; Harris, 1999; Moseley, 2007). Mirror therapy may also contribute to modulate cortical and spinal excitability (Giraux and Sirigu, 2003; Stinear and Byblow, 2004; Garry et al., 2005; Funase et al., 2007; Sakamoto et al., 2009).

Non-invasive cortical brain stimulation is another promising treatment for drug-resistant cases of neuropathic pain (Lefaucheur, 2004; Lefaucheur et al., 2004; Fregni et al., 2006). The mechanisms of action remain nuclear, but transcranial direct current stimulation (transcranial DCS) over the primary motor cortex (M1) appears to modulate cortical excitability and can reduce the intensity of neuropathic pain following a 5-day treatment trial, with both effects remaining for some time after the stimulation (Fregni et al., 2006).

DESCRIPTION OF THE INVENTION

It is necessary to offer an alternative to the state of the art which improves the results obtained thereby in the sense of diminishing the neuropathic pain some patients suffer from.

To that end, the present invention provides a method for treating neuropathic pain, comprising:
- providing, to a patient suffering from said neuropathic pain, a visual illusion to correct a mismatch between motor commands and sensory feedback; and
- applying a cranial stimulation to said patient during at least part of the duration of said visual illusion.

For an embodiment, said cranial stimulation is a transcranial stimulation, such as a transcranial direct current stimulation (tDCS), although the method is not limited to said tDCS but covers any kind of cranial stimulation a person skilled in the art would consider appropriate for the purpose of the invention, including transcranial magnetic stimulation (TMS).

For an embodiment, the method comprises applying said cranial stimulation to said patient by means of at least two stimulating non-invasive electrodes.

Depending on the embodiment, the method comprises starting the applying of said cranial stimulation a predetermined time before the providing of said visual illusion, at the same time or during the providing of said visual illusion.

For another embodiment, said applying of said cranial stimulation relates to a first session, the method comprising performing a further session of cranial stimulation after the providing of said visual illusion.

According to an embodiment, said visual illusion is provided by showing to the patient a video playing, for example on a screen.

Said video shows, for an embodiment, a body part of a person executing an action, said body part corresponding to an impaired body part of the patient.

The method further comprises providing a mirror, or any other device that can feed the patient with their own body image, in front of said patient, combined with a screen where said video is being showed, in order to show to him a combined image including a reflected non impaired body part of the patient and the video of said body part of another person.

Said neuropathic pain can comprise at least one of the next subtypes: continuous pain, paroxysmal pain, mechanical allodynia and dysaesthesia, as a consequence of any lesion at the central and/or peripheral nervous system.

As will be shown in a posterior section, where the results of a study made on a plurality of patients is shown, the beneficial effects of transcranial DCS and movement illusions is synergistic, providing results which go beyond the simple addition of the individual results achieved from said mechanisms when applied independently from each other.

BRIEF DESCRIPTION OF THE DRAWINGS

The previous and other advantages and features will be more fully understood from the following detailed description of embodiments, with reference to the attached drawings, which must be considered in an illustrative and non-limiting manner, in which.

(A) Mean values (±standard deviation) of the intensity of pain rated in the NRS at baseline in the four groups of patients.

(B) Percentage of improvement for the overall pain intensity perception in each group at the different times of evaluation following treatment. Data are shown as mean±standard error. *$P<0.005$ (Mann-Whitney U) transcranial DCS+visual illusion (VI) versus visual illusion and versus placebo. $P\le 0.05$ (Mann-Whitney U) transcranial DCS+visual illusion versus transcranial DCS, versus visual illusion and versus placebo. *$P\le 0.05$ (Mann-Whitney U) transcranial DCS+visual illusion versus transcranial DCS, versus visual illusion.

(C) Percentage of improvement for the general pain perception in each patient and mean of the group (black circle) at the last day of the treatment. Grey line, mean value of percentage improvement and confidence interval (95% CI) in the placebo group (mean 5.59; CI range, from 15.5 to −4.3).

DETAILED DESCRIPTION OF SEVERAL EMBODIMENTS

Figure 2:
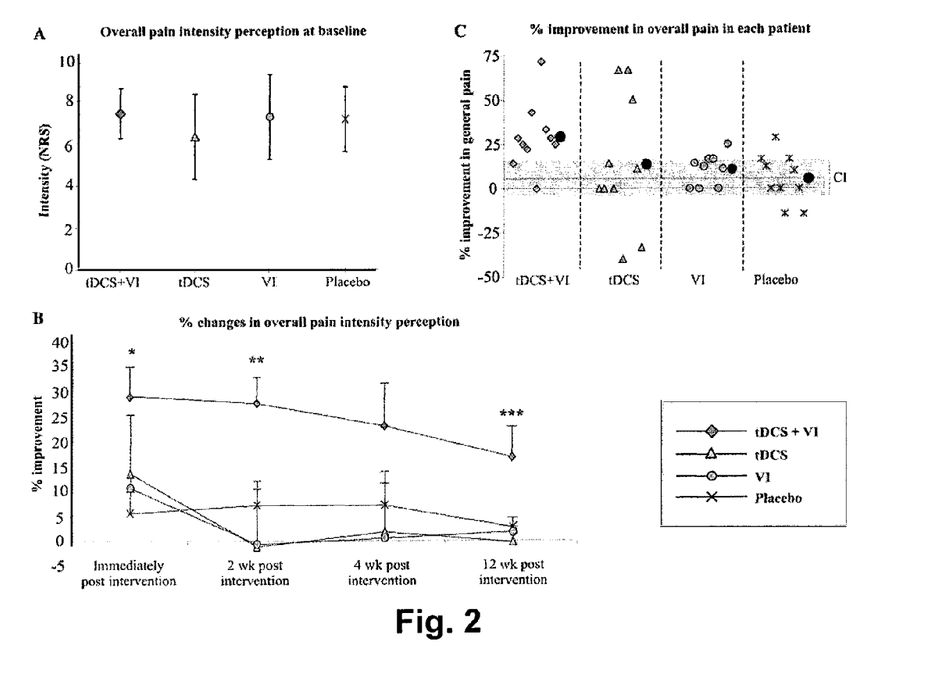
FIG. 2 shows, by means of three graphs, the results of the application of the method of the invention as per a clinical study, compared with the results obtained with conventional techniques, where.

In the present section, a study regarding a clinical evaluation of the method of the invention compared to conventional methods is described in detail, which results are shown in FIG. 2.

Figure 1:
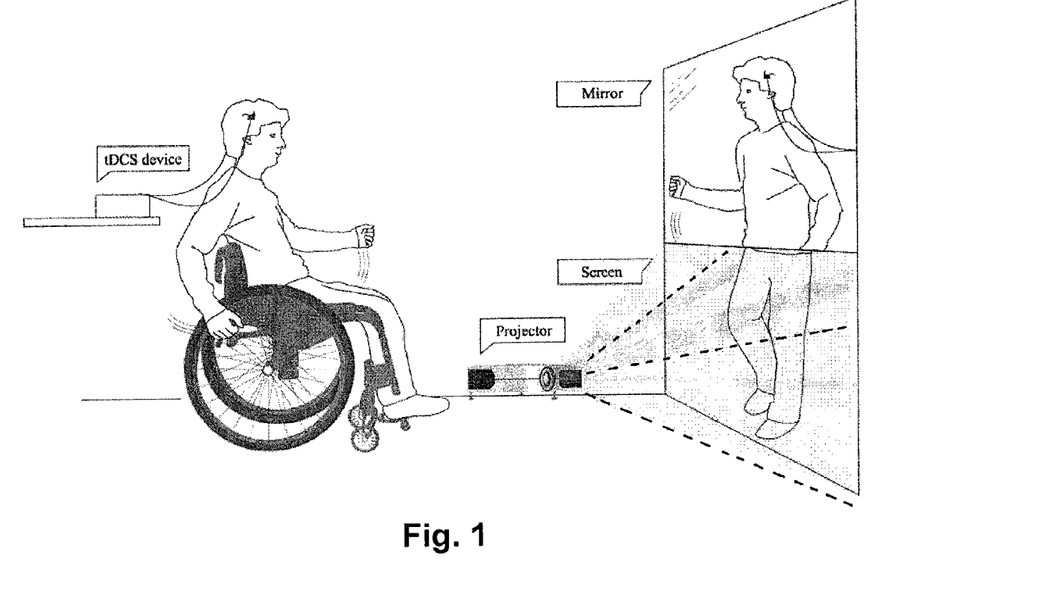
FIG. 1 is a schematic drawing of the setting used for the virtual reality procedure to induce walking visual illusion combined with a transcranial DCS, according to the method of the invention, for an embodiment.

This evaluation study was performed by using the elements shown in FIG. 1, i.e. a mirror reflecting the upper part of the patient's body placed over a screen which shows a video, by means of a projector, where the legs of another person are walking, together with a tDCS device used to apply tDCS stimulus to the patient's brain during the video watching.

The main objective of this study was to evaluate the effects of transcranial DCS alone, visual illusion alone (in the mode of 'virtual walking illusion'), or the combination of both interventions (transcranial DCS+visual illusion) in patients with neuropathic pain following SCI.

Material and Methods:
Patients:

Forty subjects with SCI evaluated at the Institute Guttmann Neurorehabilitation Hospital (Barcelona, Spain) between January 2007 and December 2008 (Table 1) were included in the study. The inclusion criteria were: (i) age over 18 years; (ii) chronic neuropathic pain at or below SCI level for at least 6 months following trauma or disease of the spinal cord; (iii) a pain intensity of at least 4 out of 10 in the numerical rating scale (NRS) at both screening (scored during the previous 24 h) and randomization; and (iv) stable pharmacological treatment for at least 2 weeks prior to the study and throughout the trial. SCI was classified using the International Standards for Neurological Classification of SCI according to neurological level (the most caudal segment of the spinal cord with normal sensory and motor function on both sides of the body) and the American Spinal Cord Injury Association Impairment scale (Marino et al., 2003).

Persistent neuropathic pain was defined as chronic pain in an area of sensory abnormality corresponding to the spinal cord lesion. Pain did not have any primary relation to spasms or any other movement and had to have started after the SCI, be present for at least 6 months and be unresponsive to adequate medication trials. Patients with severe pain of other origin, such as musculoskeletal pain, were excluded (Siddall et al., 2003). Other exclusion criteria were head trauma, alcohol or substance abuse and any other chronic medical conditions in which transcranial DCS is relatively contraindicated, such as pregnancy or epilepsy. We also excluded patients with evidence of depression (Beck Depression Inventory414 points) (Beck and Steer, 1996). The study protocol was approved by the Institutional Review Board of the Institut Guttmann and all patients gave written informed consent.

Clinical Evaluation

Outcome measures were consistent with Initiative on Methods, Measurement and Pain Assessment in Clinical Trials (IMMPACT) guidelines (Dworkin et al., 2005), and included measures of pain intensity, interference with function and global pain relief.

All patients underwent a structured interview to assess the clinical and phenomenological characteristics of the pain: location, descriptive characteristics, intensity and interference with activities of daily living, mood and sleep, as well as anxiety state.

All patients were evaluated at five time points: before treatment (baseline), at Day 14 (last day of treatment), at Day 24 (first follow-up) and at Day 38 (second follow-up) after initiation of treatment and finally, 12 weeks after treatment (third follow-up). The same researcher, who was blind to the treatment interventions, performed all clinical evaluations. A second researcher, who applied the interventions, remained blind to the findings of the clinical evaluation. Assignment of the patients to the treatment interventions was random, and patients remained blinded to their treatment condition and the specific hypotheses of the study.

The primary outcome measure was the percentage of change in average daily intensity pain score from the baseline week to the last day of treatment, first, second and third follow-up time points. Intensity pain score was assessed using a NRS. Patients were asked to rate their pain, indicating the number that best described their pain on average over the previous 24 h from 0 (no pain) to 10 (unbearable pain). The following secondary outcome measures were used.

Neuropathic Pain Symptom Inventory

This was used for the assessment of different symptoms of neuropathic pain (Bouhassira et al., 2004). We explored the localization and temporal characteristics of pain in the region of sensory loss. We categorized the pain descriptors into four main types.

(i) Continuous pain (pain that the patient felt constantly or most of the day in the deafferented area). We asked the patient to characterize the pain offering three descriptors: burning or hot, oppressive and squeezing.

(ii) Paroxystic pain (spontaneous brief crises of pain varying in duration and frequency during the day). This was described as shooting or electric current.

(iii) Mechanical allodynia. This was evaluated by moving a soft brush lightly over the skin, within the area of worse pain.

(iv) Dysaesthesia (sensation of tingling or pins and needles). The NRS was used for rating each of these categories. In the case of allodynia, the mean of three consecutive NRS measures was determined. A numerical quotation was also used for the evaluation of number of paroxysmal pain crises per day. Subtype of pain was evaluated according to the criteria defined by André-Obadia et al. (2008).

Brief Pain Inventory

The subscales measure the interference with general activity, sleep, mood, enjoyment of life, walking ability, ability to work and perform daily tasks and relationship with other people (Cleeland and Ryan, 1994). Subjects were asked to rate how their pain interfered with these items over the previous 24 h using the NRS. The score ranged from 0 (no interference) to 10 (complete interference). A modified version of the Brief Pain Inventory adapted for people with SCI was used in this study replacing 'walking ability' with 'ability to get around' (Bryce et al., 2007).

Anxiety

This was measured on a NRS ranging from 0 (no anxiety) to 10 (worst anxiety).

Patient Global Impression of Change

This was evaluated according to the method of Farrar et al. (2001).

Adverse Effects

These were evaluated using an open-ended question after each treatment session.

Experimental Design

In this double-blind, placebo-controlled trial, patients were randomly assigned to one of four treatment groups: transcranial DCS+visual illusion group, transcranial DCS+control illusion (transcranial DCS group), transcranial DCS sham+visual illusion (visual illusion group) and transcranial DCS sham+control illusion (placebo group). We used a computer-generated list as randomization strategy. We assessed patient blinding at the end of the trial by asking each patient to guess which treatment they believed to have received.

Each patient received 10 treatment sessions, 20 min each, during a period of 2 weeks (from Monday to Friday). All sessions were performed in the same quiet room, at approximately the same time of the day.

Transcranial Direct Current Stimulation

Direct current was delivered from a battery-driven, constant current stimulator (NeuroConn, Germany) using saline-soaked surface sponge electrodes (35 cm2). The anode was placed over C3 or C4 (EEG 10/20 system) to target the motor cortex (M1) and the cathode over the contralateral supraorbital area. This electrode position has previously been shown to enhance excitability of the primary motor cortex effectively (Nitsche and Paulus, 2001) and to induce pain relief (Fregni et al., 2006). For patients with asymmetric pain, stimulation was applied to the M1 contralateral to the more painful hemibody. For patients with symmetric pain, the dominant hemisphere was stimulated. A constant current of 2 mA intensity was applied for 20 min. For sham stimulation, the electrodes were placed in the same positions as for real stimulation; however, the stimulator was turned off after 30 s of stimulation so that the subjects felt the initial itching sensation, but received no current for the rest of the stimulation period. This type of sham stimulation has been shown to blind subjects reliably (Gandiga et al., 2006).

Visual Illusion

We used the setup and protocol described by Moseley (2007). During transcranial DCS (anodal or sham) the patients were sitting either in a wheelchair or in a normal chair, depending on their level of impairment, placed 2.5 m in front of a screen. After 5 min of real or sham transcranial DCS, a video was turned on, which was played on a portable computer and projected onto the screen in front of the patient. The video showed the legs of a person, either a man or a woman depending on the gender of the patient, walking on a treadmill. The video was continuously played for the remaining 15 min of the transcranial DCS session. The walking rhythm of the legs shown in the video changed in speed in a random manner to diversify the experimental condition and to hold the interest and prevent boredom of the patients. In order to induce the experience of realistic gait perception, a vertical mirror (150 cm×52 cm) was placed in front of the patients, on top of the screen, so that the mirror reflection of the upper part of the patient's own body was aligned as well as possible with the walking legs displayed on the screen. Thanks to this alignment, the patients could see themselves as if walking (in the mirror) (FIG. 1). The patients were encouraged to imagine themselves walking and, if able, to move their arms and upper body in synchrony with the walking rhythm of the legs to increase the effectiveness of the visual illusion. A synchronized sound of walking steps, matching the walking rhythm of the legs on the video, was played via loudspeakers to enhance the realism of gait perception by the patient. Moseley (2007) provided evidence that a similar setup can induce realistic gait perception, movement perception in the paralysed limbs and pain relief in patients with SCI.

Control Illusion

As a control condition for the visual illusion experience, we used a control illusion. We chose a movie containing graphical illustrations, faces or landscapes, but no images of human movement, specifically no gait actions. The control illusion covered an interesting topic so that the patients did not become bored or tired during the session. Instead of the video with the walking legs, the investigator turned on the control illusion for 15 min and the patient was told to simply watch and relax.

Statistical Analyses

Categorical variables are given as percentages. Continuous variables are represented as mean and standard deviation. Each subtype of pain was evaluated only in patients who presented that kind of pain. For general pain perception, subtypes of pain and Brief Pain Inventory items, we calculated the percentage of change at each time point of evaluation in comparison to baseline.

Normal distribution was assessed with Kolgomorov-Smirnov test. Baseline homogeneity was compared by chi-squared tests for categorical data. For multiple group comparisons and Krusskall-Wallis tests between percentage changes among different groups comparison were used for multiple group comparison, followed by a Mann-Whitney U-test for two group comparisons; the non-parametric Wilcoxon t-test was used to compare the results after treatment and follow-up with baseline values. The significance level was set at $P \leq 0.05$.

We correlated changes in pain (as indicated by change in the NRS score) with clinical characteristics, such as gender, SCI aetiology, level of the lesion, American Spinal Cord Injury Association Impairment scale classification (complete versus incomplete lesion) and time since SCI. The Pearson correlation coefficient was used to analyse the relationships between continuous variables. For categorical variables we dichotomized the mean pain changes into two groups and compared them using one-way ANOVA.

Results:

Patient Characteristics:

Forty patients were randomly assigned to one of four study groups (transcranial DCS+visual illusion, transcranial DCS, visual illusion and placebo groups). Only three patients failed to complete the entire study. One patient with tetraplegia assigned to the visual illusion group requested to stop the trial after the second session due to increased pain in his arms. This might have been due to his attempts to move the arms during visual illusion. In addition, problems in his daily transportation to the hospital contributed to the decision to stop the participation in the study. One patient in the 'transcranial DCS+visual illusion' group and one in the placebo group dropped out at the second follow-up because they moved to another city.

Demographic variables and clinical characteristics related to the lesion and pain were similar in all four groups of patients. Clinical characteristics of the patients are summarized in Table 1. The mean age was 45 years [standard deviation (SD)=15.5; range 21-66 years]. When we analysed the types of medications, no difference was found in the distribution of pharmacological treatments among the four groups.

General Pain Perception

As illustrated in FIG. 2A, baseline scores of pain intensity evaluated with the NRS were similar in the four groups (P=0.340). Table 2 summarizes the main outcomes for all the study groups across the various time-points of evaluation.

The primary outcome measure, the degree of change in pain assessed by the NRS, revealed a significant effect of intervention (FIGS. 2B and C). After the last day of treatment, the NRS of pain perception was reduced by 29.7% with respect to baseline in the transcranial DCS+visual illusion group, a significant reduction compared to visual illusion (P=0.008) and placebo groups (P=0.004). At the first follow-up, the pain reduction was significantly greater in the transcranial DCS+visual illusion than in the other three study groups: visual illusion (P=0.008), transcranial DCS (P=0.05) and placebo (P=0.009) groups. At the second follow-up, there was no difference between groups (P>0.4), but at the last follow-up (12 weeks) the percentage of improvement was again significantly different between four groups (Kruskal-Wallis; P=0.047). Specifically, patients in the transcranial DCS+visual illusion group showed greater maintenance of improvement than those in the transcranial DCS (Mann-Whitney U; P=0.052) or visual illusion groups (Mann-Whitney U; P=0.053).

Figure 3:
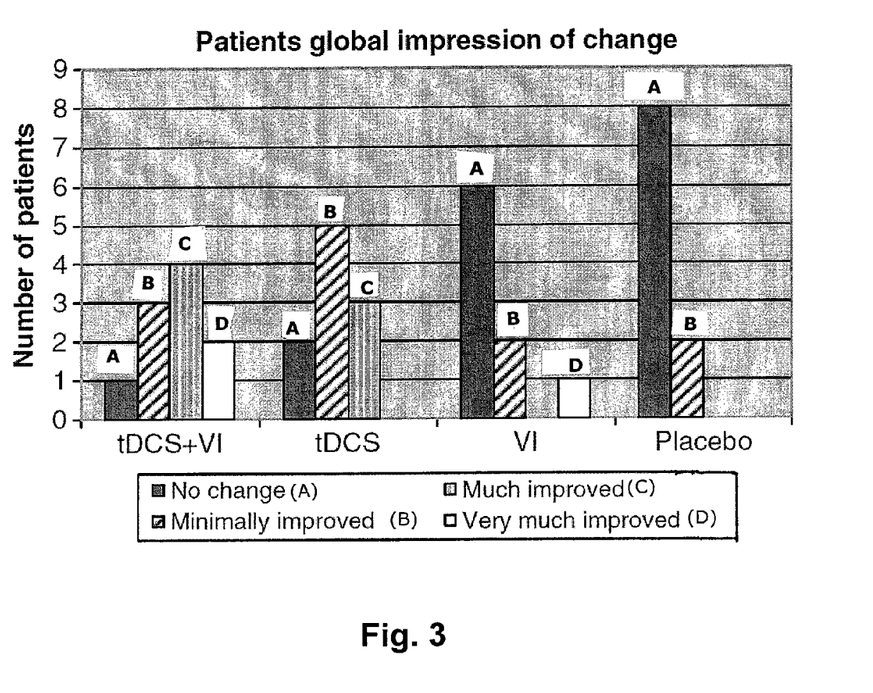
FIG. 3 shows, by means of a graph, the patient global impression of change after the last day of treatment as per the clinical study which results are shown in FIG. 2. Rated on a seven-point scale of overall change experienced by patients at the last day of treatment. VI=visual illusion.

Within each group, a statistically significant reduction in the NRS for pain was found in the transcranial DCS+visual illusion group at the last day of treatment (P=0.007) and the three follow-up evaluations in comparison to baseline values (P<0.04: Table 2). In the visual illusion group, patients revealed significant improvement in neuropathic pain intensity after the last day of treatment (P=0.02), but this effect was not maintained at the follow-up visits in comparison to baseline (P>0.5). Transcranial DCS and placebo groups did not show any significant changes (FIG. 3).

Regarding individual patient changes, it is noteworthy that three patients in the transcranial DCS+visual illusion group responded better than the best responder of the placebo group. This result appears identical in the transcranial DCS alone group (where three patients also showed such an improvement). However, in this group, two patients experienced notable worsening of the pain during the study. When considering a 30% improvement as a categorical effect size (Farrar et al., 2001; Dworkin et al., 2005, 2008), only 30% of patients in the transcranial DCS+visual illusion group and 30% in the transcranial DCS group reached this level of neuropathic pain amelioration (FIG. 2C). Another four patients in the transcranial DCS+visual illusion group (but none in the transcranial DCS group) had an improvement between 20 and 30%. In order to explore this observation further, we calculated 95% confidence intervals (CI) of overall pain intensity perception for the placebo group and analysed findings in the other groups against these reference CI. Among the patients in the transcranial DCS and visual illusion groups, 30% had a better response than the upper CI, whereas in the transcranial DCS+visual illusion group 80% of the patients showed such a favourable outcome (FIG. 2C).

Relation Between General Pain Changes and Disease Characteristics

We did not find any correlation between general pain change and age at the time of injury, age at the time of study or time since SCI. There were no significant differences in general pain change according to gender, type of SCI aetiology (medical or traumatic), level of the SCI (lumbar, thoracic or cervical) or SCI severity (complete or incomplete) for the whole population of patients included in the study.

Changes in Subtypes of Neuropathic Pain

Whereas most patients (29 of 39) complained of continuous pain, 22 patients also reported paroxysmal pain, 26 mechanical allodynia and 26 spontaneous dysaesthesias. There were no significant differences between groups regarding the severity of these subtypes of neuropathic pain symptoms, except dysaesthesias, which were more severe at baseline in the transcranial DCS+visual illusion and visual illusion groups than in the transcranial DCS and placebo groups (P<0.05) (Table 2).

Continuous Pain

The percentage of change in continuous pain score did not show any significant difference between the four groups at any time point of evaluation (P>0.06).

Within group changes over time revealed a significant effect of transcranial DCS+visual illusion, transcranial DCS and visual illusion treatments on amelioration of continuous pain scores after the last day of treatment (P=0.041, 0.012 and 0.018, respectively), but this effect was not maintained at the first and second follow-up examinations in any of the groups (P>0.08).

Paroxysmal Pain

After the last day of treatment, the percentage change in paroxysmal pain was significantly greater in the transcranial DCS+visual illusion group compared with the placebo group (P=0.048), but not compared with the transcranial DCS (P=0.75) or visual illusion (P=0.28) groups. The same comparison with the placebo group was still significant at the first follow-up (P=0.008), but not at the second follow-up.

When the change in paroxysmal pain was compared at each time point within each group, there was a significant improvement in the transcranial DCS+visual illusion (P=0.02) and transcranial DCS (P=0.007) groups comparing baseline values. The effect maintained at the last day of treatment and the first and second follow-up evaluations in the transcranial DCS+visual illusion (P<0.04) and transcranial DCS (P<0.03) groups for both comparisons.

Daily number of pain crises decreased significantly in the transcranial DCS+visual illusion group after treatment and at first follow-up in comparison to baseline (12.8±14.1 at baseline; 4.3±6.1 last day of treatment; 4.6±3.1 first follow-up; P<0.02), but not at the second follow-up (7.6±9.0). In the group with transcranial DCS, the number of pain crises was significantly reduced after treatment (P=0.045) but not at the first and second follow-up visits (6.1±7.8 baseline; 3.1±6.1 last day of treatment; 4.2±6.3 first follow-up; 4.2±6.1 second follow-up). The visual illusion and placebo groups did not reveal significant changes in the frequency of pain crises.

Mechanical Allodynia

At the last day of treatment and the first follow-up, the percentage changes in mechanical allodynia were not significantly different between the four groups (Kruskal-Wallis; P=0.16 and 0.24). At the second follow-up, the percentage reduction of mechanical allodynia was significantly greater in the transcranial DCS+visual illusion compared with the visual illusion (P=0.05) and the placebo (P=0.009) groups.

Within group changes, only the transcranial DCS+visual illusion group showed a significant improvement the last day of treatment and at the first follow-up in comparison to baseline (P<0.02 at each time point) (Table 2).

Dysaesthesias

The percentage changes in dysaesthesias were not significantly different between the four groups at last day of the treatment and first follow-up (Kruskal-Wallis; P>0.1), but at the second follow-up, the improvement in dysaesthesias was significantly greater in the transcranial DCS+visual illusion group (P=0.04) and in the visual illusion group (P=0.03) compared to the placebo.

Within group comparisons indicated that the transcranial DCS+visual illusion group had a significant improvement in dysaesthesias at the last day of the treatment, first and second follow-up visits (P=0.03) as compared with baseline. The visual illusion group showed a significant improvement at the last day of the treatment and the second follow-up (P=0.04).

Interference with Activities of Daily Living Due to Changes in Pain

The mean scores from the Brief Pain Inventory questionnaire of each of the four groups at the evaluated time points are shown in Table 3. In general, the transcranial DCS+visual illusion group showed the highest improvement at the end of the treatment and during the follow-up. At the last day of the treatment, there were significant improvements in the percentage changes of enjoyment in the transcranial DCS+visual illusion group compared to the transcranial DCS group (P=0.04), and in the percentage changes in the ability to get around, the ability to work and perform daily tasks, the relationships with others, the interference of pain in sleep and enjoyment in the transcranial DCS+visual illusion group compared to the visual illusion group (P≤0.05 for all comparisons). At the first follow-up this improvement was maintained in the ability to work and perform daily tasks and in enjoyment in the transcranial DCS+visual illusion group compared to visual illusion group (P≤0.05). At the second follow-up, the ability to get around continued to be better in the transcranial DCS+visual illusion group than in the visual illusion group (P=0.05).

When comparing the transcranial DCS+visual illusion group with the placebo group, we found significant improvements in the percentage changes in mood, the ability to work and perform daily tasks, interference of pain in sleep and enjoyment at the last day of the treatment (P≤0.05 for all comparisons), in general activity, ability to get around, the ability to work and perform daily tasks, interference of pain in sleep and enjoyment at the first follow-up (P<0.05).

Group transcranial DCS also showed more improvement in the ability to get around than visual illusion group (P=0.04) on the last day of the treatment, and greater improvement in general activity at the second follow-up than the visual illusion (P=0.006) and placebo (P=0.01) groups. At the last day of the treatment, there was significant improvement in the percentage changes in interference of pain in sleep in the visual illusion group than the placebo group (P=0.05) (Table 3).

When changes in each parameter along time, within each group were compared, patients in the transcranial DCS+visual illusion group showed significant improvement with respect to baseline in pain interference with general activity and the ability to work and perform daily tasks at the three time-points of evaluation. There was also a significant beneficial effect on the interference of pain with sleep, the ability to get around and enjoyment of life in this group at the last day of treatment and the first follow-up as compared with baseline.

In the transcranial DCS group, the general activity and the ability to get around in relation with pain interference improved significantly only at the last day of the treatment. All four groups showed significant improvement with respect to pain interference with mood at the last day of treatment (transcranial DCS+visual illusion P=0.028, transcranial DCS P=0.01, visual illusion P=0.026 and placebo P=0.024). In the visual illusion and placebo groups none of the other variables changed significantly over time.

Changes in the Anxiety Scale

Baseline scores for anxiety on the NRS were similar among the four groups (P=0.340). Anxiety decreased significantly after the last day of treatment in the transcranial DCS+visual illusion, transcranial DCS and visual illusion groups (P<0.019) in comparison to baseline levels. This improvement was maintained at the first and the second follow-up visits only in the transcranial DCS+visual illusion group (P<0.04). The placebo group did not show any significant changes.

Self-Reported Pain Relieving Effect of Treatment

All patients rated the pain relieving effect of the treatment using the patient global impression of change (FIG. 3) after the last day of treatment. Five patients in the transcranial DCS+visual illusion (50%), three in the transcranial DCS (30%) and one in visual illusion (11%) groups rated pain as markedly improved ('much improved' or 'very much improved'), whereas only two patients of the placebo group (20%) rated their pain as improved and then only as 'minimally improved'. The between-group difference was statistically significant (P=0.013).

Tolerability and Safety

Three patients complained of mild headache during some of the active transcranial DCS sessions (mainly during the first session) but none described this side effect as seriously unpleasant, none considered discontinuing study participation (even though it was explicitly offered) and in all instances the discomfort disappeared within 2-3 h after the session finished.

Another three patients reported feeling tired after being engaged in fictive locomotion for the first time, and one patient with incomplete SCI reported a transient increase in neuropathic pain. These symptoms may have been due to focused attention and unaccustomed movements of the upper body executed during 15 min. One patient had to discontinue the movement during visual illusion because of musculoskeletal pain in the upper extremities. All these minor side effects disappeared after the end of the session and none of the patients indicated significant distress. As mentioned above, the one patient with increased neuropathic pain discontinued participation in the study, but in good measure this was due to the difficulties in securing reliable transportation to the hospital rather than solely due to the discomfort.

Assessment of Blindness

At the end of the treatment sessions none of the patients could tell whether they had undergone real or sham transcranial DCS, even when explicitly asked. Force choice was at random level and there was no correlation between correct or incorrect guessing and any of the results described above.

Discussion:

The present double blind, placebo-controlled study provides evidence that the combination of transcranial DCS and visual illusion significantly reduces neuropathic pain, continuous pain, paroxysmal pain, mechanical allodynia and dysaesthesias in patients with SCI, and can reduce the interference of pain with activities of daily living. We found that each isolated intervention also had some desirable effect: transcranial DCS resulted in an improvement in paroxysmal pain but no significant improvement in overall pain intensity, whereas in the visual illusion group improvement was significant for overall pain, continuous pain and dysaesthesias. The greater beneficial effect on the overall pain intensity perception was achieved despite the fact that at baseline, the mean subjective NRS of pain was highest for the transcranial DCS+visual illusion group, although the differences across groups were not statistically significant. The effects of the combined intervention on the overall pain intensity perception were also longer lasting that those of the other interventions in most of the clinical scales: after 10 treatment sessions two groups (transcranial DCS+visual illusion and visual illusion groups) experienced an initial reduction in the NRS pain score, but at the first follow-up evaluation patients in the transcranial DCS+visual illusion group maintained the improvement whereas there was a loss of efficacy in the visual illusion group. At the second and third follow-up evaluations, 4 and 12 weeks after treatment, respectively, the combined treatment group still presented a significant improvement, whereas there were no significant changes with respect to baseline in the other three groups.

In addition to the analgesic effect, the combined transcranial DCS+visual illusion intervention also showed greater effect than the other three interventions on pain interference with activities of daily living and anxiety. Anxiety is closely linked to pain perception. Anxiety may contribute to the perception of pain and can exacerbate pain. On the other hand, perceptions of pain also cause anxiety. It is thus difficult to establish whether our interventions primarily affected anxiety and secondarily changed pain, or vice versa. In our study, the three active conditions (transcranial DCS+visual illusion, transcranial DCS and visual illusion) induced a reduction in the anxiety scores, with a slight advantage of the combined treatment group where the anxiety level continued to be decreased at follow-up. No reduction in anxiety score was found in the placebo group, thus controlling for the possibility that anxiety reduction could be simple related participation in the study. We speculate that the reduction in anxiety in the active intervention groups, particularly in the transcranial DCS+visual illusion group, is related to the reduction in chronic neuropathic pain. However, a direct, independent effect on anxiety cannot be ruled out. The effects on the activities of daily living are likely to reflect the combined impact on neuropathic pain and anxiety, but our study was not designed to disentangle the relative contributions of each factor.

Subtypes of Neuropathic Pain Differentially Responded to Treatment

Neuropathic pain is a heterogeneous condition manifesting with a variety of symptoms (Finnerup et al., 2005; André-Obadia et al., 2008) and it is important to evaluate the subtypes of clinical neuropathic pain, because different pain subtypes may reflect different pathophysiological mechanisms (Attal et al., 2008; Costigan et al., 2009) requiring differential therapeutic interventions (Cruccu and Truini, 2009).

Our results demonstrate that each active treatment (transcranial DCS+visual illusion, transcranial DCS and visual illusion) had analgesic effects to variable degrees on different subtypes of neuropathic pain, while the placebo intervention had none Table 2). Continuous pain improved in patients exposed to transcranial DCS+visual illusion, transcranial DCS and visual illusion just after treatment. Paroxysmal pain improved, in terms of intensity and number of pain crises, in patients exposed to transcranial DCS+visual illusion and transcranial DCS and the benefit lasted for 30 days after the end of the treatment. Mechanical allodynia was only clearly improved in the transcranial DCS+visual illusion group and dysaesthesias in the transcranial DCS+visual illusion and visual illusion groups. These observations suggest that transcranial DCS alone and visual illusion alone or in combination are therapeutic strategies that may be tailored to different types of neuropathic pain patients. Future studies might be designed to capture within patient effects in order to assess these important aspects further.

Effect of Transcranial Direct Current Stimulation

Anodal transcranial DCS is associated with an increase of cortical excitability that lasts beyond the stimulation period (Nitsche and Paulus, 2001; Nitsche et al., 2005). Physiologic studies dating back to the 1960s suggest that transcranial DCS induces changes in neuronal membrane potential due to shifts in extracellular ion concentration (Nitsche et al., 2003). Thus, transcranial DCS is thought to be a purely neuromodulatory intervention promoting synaptic plastic changes in response to combined inputs (Wagner et al., 2007). Upregulation of motor cortex excitability might modify pain perception through indirect effects on pain-modulating areas, such as thalamic nuclei. Garcia-Larrea et al. (1999) proposed the 'thalamus pain-related structure pathway' as the substrate for pain relief induced by motor cortex stimulation. Positron emission tomography in patients undergoing epidural electrical motor cortex stimulation seems to trigger rapid and phasic activation in the lateral thalamus, which leads to a cascade of events of longer time-course in medial thalamus, anterior cingulated/orbitofrontal cortices and upper brainstem (Peyron et al., 2007). Changes of thalamic activity are also associated with stimulation of the motor cortex by transcranial magnetic stimulation (Strafella et al., 2004) and transcranial DCS (Lang et al., 2005). Because of the large electrode size, transcranial DCS is likely to have induced excitability modulation over a large area centred around the motor cortex and encompassing cortical areas representing the painful body segments. This may explain why in this study transcranial DCS applied to the motor cortex was effective in patients with neuropathic pain affecting different body parts, including lower limbs and trunk.

The finding that transcranial DCS, alone or combined with visual illusion, has a particularly strong impact on paroxysmal pain deserves further investigation into the mechanisms of action. The development of neuropathic pain after peripheral and SCI has been related to interruption of descending inhibitory tracts, loss of spinal inhibitory systems, changes in excitability of nociceptive projecting neurons and central sensitization (Woolf, 2004; Finnerup et al., 2007; Costigan et al., 2009). The short-term, activity-dependent form of central sensitization, which is produced only following activation of nociceptive pathways, is considered responsible for generating pinprick hyperalgesia and dynamic allodynia, whereas the long-term potentiation phenomena could be related to long-term excitability and continuous pain sensations. Because transcranial DCS can modulate cortical excitability, it is tempting to speculate that its effects might be due to short-term suppression of the impact of bursting afferent activity. Further studies in humans and suitable animal models are needed.

Our findings are consistent with the results of Fregni et al. (2006), who found that transcranial DCS in patients with SCI and pain paroxysms had a significantly greater reduction in their pain scores compared to patients with only continuous pain. It is worth noting, however, that the mean decrease in neuropathic pain intensity was higher in the study of Fregni et al. (2006) as compared with the results of the transcranial DCS group in the present study. The reason for this is not completely clear. Since the methodology for transcranial DCS was essentially the same in both studies, we can only speculate that the differences in characteristics of the patients are the possible explanation for the differential results. Indeed, the severity of SCI has been shown to variably influence hyperalgesia responses in experimental models (Yoon et al., 2004; Knerlich-Lukoschus et al., 2008; Redondo et al., 2009). In the present study we established inclusion criteria more specifically related to neuropathic pain according to the International Association for the Study of Pain (IASP). In addition, we took great care in carefully characterizing the patients and applied specific and stringent inclusion and exclusion criteria aimed to study patients with different pain subtypes.

Effect of Visual Illusion

Studies of visual illusion in humans have shown that observation of a movement can affect corticospinal excitability and motor performance (Gangitano et al., 2001; Maeda et al., 2002; Garry et al., 2005; Kumru et al., 2008). Brain imaging has demonstrated that movement imagery—during which subjects simply imagine making a body movement-activates many of the same regions activated by movement itself, including the primary motor cortex (Pascual-Leone et al., 1994, 2005). Kumru et al. (2008) proposed that imagining the performance of an action may lead to a transient enhancement in excitability of corticospinal projections and a reduction in intracortical inhibition in the motor cortex that is time-locked to the onset of the imagined muscle activity. Recently, Sakamoto et al. (2009) have shown that combining observation and imagery of an action further enhances corticospinal excitability as compared with what occurs during observation or imagery alone. Activity of the mirror neuron system may contribute to the increased effect of combining observation and imagery. Functional MRI studies have demonstrated that the areas activated during execution, observation and imagery of movements include overlapping loci in the dorsal premotor and superior parietal cortex where the frontoparietal mirror neuron systems are thought to exist (Filimon et al., 2007).

The ability to perform motor imagery is preserved in SCI subjects and can evoke even stronger activation of motor cortex as that seen in healthy controls (Alkadhi et al., 2005). Movement imagery of paralysed body parts in patients with SCI increases activity in the same brain regions as in healthy subjects, including primary motor cortex (Cramer et al., 2005). Enzinger et al. (2008) and Hotz-Boendermarker et al. (2008) observed robust primary sensorimotor cortex activity within the expected somatotopy in patients with SCI when imagining movement.

Recently, two studies have analysed the effect of movement imagery techniques in patients with SCI with neuropathic pain, with conflicting results. The first study demonstrated a significant reduction in neuropathic pain induced by visual illusion of walking in patients with cauda equina injury (Moseley, 2007). In the study by Moseley (2007), the patients performed a single mirror visual feedback procedure. However, Gustin et al. (2008) reported exacerbation of pain in response to imagined movements in six of seven subjects with neuropathic pain following complete thoracic SCI. In this study the subjects undertook movement imagery training (performance of a movement imagery which also involved the sound). The different results between these studies may be due to the lesion level in the patients included, and also to the application of different cognitive strategies (illusion versus imagery of movement and associated sound) that can imply different neurological mechanisms (Chan et al., 2007). The underlying mechanisms accounting for the success of such therapies remain to be elucidated.

Our results did not show marked improvement of neuropathic pain in the visual illusion group. We can speculate that the duration of therapy with visual illusion techniques alone may need to be longer than the relatively short period of time we applied. Previous studies reporting a beneficial effect of visual illusion on pain applied visual illusion treatment for a longer time, i.e. 3-8 weeks (Chan et al., 2007; Moseley, 2007; MacIver et al., 2008).

Effect of Combined Treatment

Our subjects were instructed to watch a movie of walking legs and actively promote imagery of gait. Observation and imagery of movements enhances corticospinal excitability beyond either observation or imagery alone (Sakamoto et al., 2009), and leads to greater reduction of intracortical inhibition (Kumru et al., 2008). On the other hand, anodal transcranial DCS is associated with an increase of cortical excitability (Nitsche and Paulus, 2001; Nitscheet al., 2003). Thus, in the transcranial DCS+visual illusion combined intervention, we predicted synergistic effects. Consistent with this hypothesis, we found the most significant and long-lasting analgesic benefits in this combined intervention group. However, the actual mechanisms of action remain to be elucidated.

CONCLUSION AND IMPLICATIONS

In conclusion, our results demonstrate that transcranial DCS combined with visual illusion can be effective in the management of neuropathic pain following SCI. The benefits of this combined intervention were better and longer lasting than either intervention alone (transcranial DCS or visual illusion alone). The combined intervention was effective for reduction of the overall severity of neuropathic pain and various neuropathic pain subtypes (continues and paroxysmal pain, mechanical allodynia and dysaesthesias). These beneficial effects were achieved with minimal side effects and with good tolerability. Our results corroborate and extend previous findings about the analgesic effect of transcranial DCS (Fregni et al., 2006) and visual illusion (Moseley, 2007) alone, supporting the potential usefulness of these interventions in the care of patients with SCI. Future, larger and multi-centre trials are needed to assess fully the role of these interventions in the clinical management of the neuropathic pain after SCI. Challenges that remain include exploring the best parameters and timing of stimulation, optimizing the interventions for individual patients, and examining how to extend the duration of analgesic effects and how to maintain improvement in the long term. Further studies are also needed to investigate the mechanisms of action of transcranial DCS and visual illusion. At a more conceptual level, our findings show the potential advantages of combining rehabilitation strategies with non-invasive brain stimulation technique to optimize outcome.

A person skilled in the art could introduce changes and modifications in the embodiments described without departing from the scope of the invention as it is defined in the attached claims.

TABLE 1

| Clinical and demographical characteristics of patients and medication intake | | | | | | | | |
|---|---|---|---|---|---|---|---|---|
| Patient | | | | Years | Neurological | | | |
| Sex | Age (years) | Aetiology | ASIA | since SCI | level of injury | Pain location | Type of pain | Pain medication |
| Transcranial DCS + visual illusion group | | | | | | | | |
| M | 63 | T | B | 4 | C7 | Thoracic, arms, lower limb | At and below | PGB, PCT |
| M | 38 | T | A | 3 | C6 | Abdomen, bilateral foots | Below | PGB, CNZ |
| M | 34 | T | B | 3 | C4 | Bilateral foots | Below | ANT, PGB, CNZ |

TABLE 1-continued

Clinical and demographical characteristics of patients and medication intake

| Sex | Age (years) | Aetiology | ASIA | Years since SCI | Neurological level of injury | Pain location | Type of pain | Pain medication |
|---|---|---|---|---|---|---|---|---|
| F | 36 | T | A | 2 | C4 | Arms | At | GBP |
| M | 21 | T | A | 4 | TH4 | Thoracic, lower limb | At and below | GBP, CNZ, FE |
| M | 66 | T | A | 31 | TH11 | Bilateral lower limb | Below | CNZ, GBP, ANT |
| M | 37 | ME | A | 1 | TH12 | Abdomen | At | GBP |
| M | 40 | T | A | 2 | TH10 | Lower limb, foot | Below | GBP, CNZ |
| F | 44 | ME | A | 5 | TH3 | Abdomen, lower limb | Below | ANT |
| M | 46 | ME | A | 1 | TH3 | Bilateral foots | Below | GBP, ANT |
| | | | | | | Transcranial DCS group | | |
| M | 36 | T | A | 5 | TH10 | Bilateral lower limbs | Below | TMD, CNZ, GBP |
| M | 43 | T | A | 19 | TH10 | Abdomen, lower limb | Below | PGB |
| M | 50 | T | A | 18 | TH9 | Bilateral lower limb | Below | CNZ, TMD |
| M | 28 | T | A | 2 | TH10 | Abdomen, bilateral lower limb | At and below | PCT, ANT |
| M | 32 | ME | A | 8 | TH10 | Lower limb | Below | PGB, ANT |
| M | 36 | T | A | 2 | TH9 | Lower limbs | Below | KTM, GBP, PGB, CNZ, ANT |
| M | 29 | T | A | 8 | TH8 | Genital area | Below | ANT |
| F | 49 | ME | B | 2 | C7 | Abdomen, bilateral lower limb | Below | CNZ, PGB |
| M | 44 | T | B | 3 | TH12 | Bilateral lower limb, foots | Below | TMD, CNZ, GBP |
| M | 62 | T | A | 19 | TH11 | Lower limbs | Below | GBP, CNZ |
| | | | | | | Visual illusion group | | |
| M | 57 | ME | A | 29 | TH9 | Abdomen, lower limb | At and below | PGB |
| M | 53 | ME | B | 9 | TH6 | Thoracic, lower limb | At and below | GBP, PGB |
| M | 59 | T | A | 1 | C4 | Bilateral Arms, abdomen | At and below | TMD, GBP, ANT |
| M | 42 | T | A | 25 | TH7 | Abdomen, bilateral lower limb | Below | — |
| M | 58 | T | A | 5 | TH12 | Genital area, lower limb | Below | PGB, OXT, CNZ |
| M | 35 | T | A | 9 | TH4 | Abdomen, bilateral lower limb | Below | GBP, PGB, ANT, FE |
| F | 49 | T | A | 12 | TH3 | Abdomen, bilateral lower limb | Below | FE, ANT |
| F | 27 | ME | B | 2 | TH12 | Lower limbs | Below | PGB |
| F | 57 | T | A | 6 | TH11 | Abdomen, lower limb | Below | FE, GBP, ANT |
| | | | | | | Placebo group | | |
| M | 39 | T | A | 5 | C7 | Abdomen, lower limb | Below | GBP, CNZ, FE, PGB, ANT |
| F | 50 | T | A | 2 | C5 | Lower limb, bilateral foots | Below | GBP, ANT |
| M | 58 | T | A | 4 | TH11 | Abdomen, lower limb | At and below | PGB, CNZ |
| M | 38 | T | A | 7 | TH5 | Bilateral lower limb, foot | Below | GBP, CNZ, FE |
| M | 29 | T | A | 5 | TH6 | Thoracic, lower limb | At and below | CNZ, PGB, TMD |
| M | 62 | T | A | 10 | TH11 | Lower limb | Below | PGB, GBP, CNZ, TMD |
| M | 34 | T | A | 10 | TH11 | Abdomen, bilateral lower limb | Below | CNZ, ANT, GBP, TMD |
| F | 44 | ME | B | 8 | C3 | Lower limb | Below | GBP, CNZ, ANT |
| F | 55 | T | B | 21 | C7 | Abdomen, arms | At and below | — |
| M | 41 | ME | A | 14 | TH10 | Lower limb | Below | GBP |

M = male; F = female. Aetiology: T = trauma; ME = medical aetiology. ASIA classification: A = complete, no sensory or motor function is preserved in the sacral segments S4-S5; B = incomplete, preservation of sensory but not motor function. Neurological level: C = cervical; TH = thoracic level SCI. Below-level pain was defined as neuropathic pain present more than three dermatomes below the neurological level equal and at-level pain as pain located within the dermatome at and three dermatomes below the neurological level. Below-level pain extending to the at-level area is classified as below-level pain if the patient is unable to distinguish two separate pain problems. Medication: GBP = gabapentin; CNZ = clonazepam; PGB = pregabalin; TMD = tramadol; FE = fentanyl; KTM = ketamine; OXT = oxycodone; ANT = antidepressive.

TABLE 2

Primary and secondary outcome measures at each point of evaluation in the four groups treatment groups according to numerical rating scale

| Evaluation | Baseline | Last day | First follow-up | Second follow-up |
|---|---|---|---|---|
| Transcranial DCS + visual illusion group | | | | |
| Overall pain | 7.5 ± 1.2 | 5.2 ± 1.5* | 5.3 ± 1.4* | 5.5 ± 1.8* |
| Continuous pain (n = 8) | 7.0 ± 2.5 | 4.6 ± 2.4* | 5.0 ± 2.3 | 5.3 ± 0.8 |
| Paroxysmal pain (n = 7) | 8.5 ± 2.3 | 3.3 ± 2.6* | 5.3 ± 2.3* | 5.5 ± 3.2* |
| Allodynia (n = 7) | 5.9 ± 2.8 | 2.6 ± 2.4* | 1.7 ± 2.1* | 2.8 ± 3.3 |
| Dysesthesia (n = 9) | 6.8 ± 1.7 | 5.0 ± 1.7* | 5.3 ± 1.7* | 5.1 ± 1.8* |
| Transcranial DCS group | | | | |
| Overall pain | 6.3 ± 2.0 | 5.3 ± 2.6 | 6.1 ± 2.5 | 5.9 ± 2.3 |
| Continuous pain (n = 8) | 7.0 ± 3.5 | 4.1 ± 3.5* | 5.9 ± 4.1 | 5.1 ± 3.9 |
| Paroxysmal pain (n = 6) | 8.8 ± 1.5 | 4.5 ± 3.1* | 6.0 ± 3.7 | 6.7 ± 3.3* |
| Allodynia (n = 5) | 5.5 ± 2.6 | 5.0 ± 2.4 | 5.3 ± 2.1 | 6.3 ± 3.5 |
| Dysesthesia (n = 4) | 4.3 ± 1.0 | 4.5 ± 1.3 | 4.5 ± 1.0 | 3.0 ± 2.6 |

TABLE 2-continued

Primary and secondary outcome measures at each point of evaluation in the four groups treatment groups according to numerical rating scale

| Evaluation | Baseline | Last day | First follow-up | Second follow-up |
| --- | --- | --- | --- | --- |
| Visual illusion group | | | | |
| Overall pain | 7.2 ± 1.6 | 6.4 ± 1.6* | 7.2 ± 1.5 | 7.1 ± 1.4 |
| Continuous pain (n = 7) | 8.4 ± 1.5 | 4.9 ± 1.9* | 7.6 ± 2.4 | 8.4 ± 2.3 |
| Paroxysmal pain (n = 4) | 8.0 ± 1.4 | 5.7 ± 1.5 | 6.7 ± 1.7 | 6.7 ± 1.2 |
| Allodynia (n = 6) | 6.8 ± 2.5 | 4.6 ± 1.9 | 6.6 ± 2.3 | 6.0 ± 3.5 |
| Dysesthesia (n = 5) | 7.4 ± 1.8 | 4.4 ± 2.7* | 6.2 ± 1.5 | 5.4 ± 1.8* |
| Placebo group | | | | |
| Overall pain | 7.1 ± 1.5 | 6.6 ± 1.9 | 6.4 ± 1.9 | 6.6 ± 1.8 |
| Continuous pain (n = 6) | 7.0 ± 1.5 | 6.5 ± 1.9 | 6.2 ± 2.4 | 7.0 ± 2.3 |
| Paroxysmal pain (n = 5) | 8.0 ± 1.4 | 7.8 ± 1.5 | 8.5 ± 1.7 | 8.0 ± 1.2 |
| Allodynia (n = 8) | 5.4 ± 2.3 | 4.4 ± 1.8 | 4.4 ± 2.3 | 5.6 ± 2.1 |
| Dysesthesia (n = 8) | 5.1 ± 1.8 | 3.1 ± 2.4 | 4.5 ± 2.3 | 4.9 ± 1.5 |

*$P < 0.05$ with respect to baseline values at entry into the study.

REFERENCES

Alkadhi H, Brugger P, Boendermaker S H, Crelier G, Curt A, Hepp-Reymond M C, et al. What disconnection tells about motor imagery: evidence from paraplegic patients. Cereb Cortex 2005; 15: 131-40.

Andre-Obadia N, Mertens P, Gueguen R, Peyron R, Garcia-Larrea L. Pain relief by rTMS: Differential effect of current low but no specific action on pain subtypes. Neurology 2008; 71: 833-40.

Attal N, Fermanian C, Fermanian J, Lanteri-Minet M, Alchaar H, Bouhassira D. Neuropathic pain: are there distinct subtypes depending on the aetiology or anatomical lesion? Pain 2008; 138: 343-53.

Beck A T, Steer R, editors. Beck Depression Inventory-II. San Antonio, Tex.: Psychological Corporation; 1996.

Bouhassira D, Attal N, Fermanian J, Alchaar H, Gautron M, Masquelier E, et al. Development and validation of the neuropathic pain symptom inventory. Pain 2004; 108: 248-57.

Bryce T N, Budh C N, Cardenas D D, Dijkers M, Felix E R, Finnerup N B, et al. Pain after spinal cord injury: an evidence-based review for clinical practice and research. Report of the National Institute on Disability and Rehabilitation Research Spinal Cord Injury Measures meeting. J Spinal Cord Med 2007; 30: 421-40.

Cleeland C S, Ryan K M. Pain assessment: global use of the Brief Pain Inventory. Ann Acad Med Singapore 1994; 23: 129-38.

Costigan M, Scholz J, Woolf C J. Neuropathic pain: a maladaptive response of the nervous system to damage. Annu Rev Neurosci 2009; 32: 1-32.

Chan B L, Witt R, Charrow A P, Magee A, Howard R, Pasquina P F, et al. Mirror Therapy for phantom limb pain. N Engl J Med 2007; 357: 2206-7.

Cramer S C, Lastra L, Lacourse M G, Cohen M J. Brain motor system function after chronic, complete spinal cord injury. Brain 2005; 128: 2941-50.

Cruccu G, Truini A. Sensory profiles: a new strategy for selecting patients in treatment trials for neuropathic pain. Pain 2009; 146: 5-6.

Dworkin R H, Turk D C, Farrar J T, Haythornthwaite J A, Jensen M P, Katz N P, et al. IMMPACT. Core outcome measures for chronic pain clinical trials: IMMPACT recommendations. Pain 2005; 113: 9-19.

Dworkin R H, Turk D C, Wyrwich K W, Beaton D, Cleeland C S, Farrar J T, et al. Interpreting the clinical importance of treatment outcomes in chronic pain clinical trials: IMMPACT recommendations. J Pain 2008; 9: 105-21.

Enzinger C, Ropele S, Fazekas F, Loitfelder M, Gorani F, Seifert T, et al. Brain motor system function in a patient with complete spinal cord injury following extensive brain-computer interface training. Exp Brain Res 2008; 190: 215-23.

Farrar J T, Young J P Jr, LaMoreaux L, Werth J L, Poole R M. Clinical importance of changes in chronic pain intensity measured on an 11-point numerical pain rating scale. Pain 2001; 94: 149-58.

Filimon F, Nelson J D, Hagler D J, Sereno M I. Human cortical representations for reaching: mirror neurons for execution, observation, and imagery. Neuroimage 2007; 37: 1315-28.

Finnerup N B, Otto M, McQuay H J, Jensen T S, Sindrup S H. Algorithm for neuropathic pain treatment: an evidence based proposal. Pain 2005; 118: 289-305.

Finnerup N B, Sørensen L, Biering-Sørensen F, Johannesen I L, Jensen T S. Segmental hypersensitivity and spinothalamic function in spinal cord injury pain. Exp Neurol 2007; 207: 139-49.

Fregni F, Boggio P S, Lima M C, Ferreira M J, Wagner T, Rigonatti S P, et al. A sham-controlled, phase II trial of transcranial direct current stimulation for the treatment of central pain in traumatic spinal cord injury. Pain 2006; 122: 197-209.

Funase K, Tabira T, Higashi T, Liang N, Kasai T. Increased corticospinal excitability during direct observation of self-movement and indirect observation with a mirror box. Neurosci Lett 2007; 419: 108-12.

Gandiga P C, Hummel F C, Cohen L G. Transcranial DC stimulation (tDCS): a tool for double-blind sham-controlled clinical studies in brain stimulation. Clin Neurophysiol 2006; 117: 845-50.

Gangitano M, Mottaghy F M, Pascual-Leone A. Phase-specific modulation of cortical motor output during movement observation. Neuroreport 2001; 12: 1489-92.

Garcia-Larrea L, Peyron R, Mertens P, Gregoire M C, Lavenne F, Le Bars D, et al. Electrical stimulation of motor cortex for pain control: a combined PET-scan and electrophysiological study. Pain 1999; 83: 259-73.

Garry M I, Loftus A, Summers J J. Mirror, mirror on the wall: viewing a mirror reflection of unilateral hand movements facilitates ipsilateral M1 excitability. Exp Brain Res 2005; 163: 118-22.

Giraux P, Sirigu A. Illusory movements of the paralyzed limb restore motor cortex activity. Neuroimage 2003; 20: 107-11.

Gustin S M, Wrigley P J, Gandevia S C, Middleton J W, Henderson L A, Siddall P J. Movement imagery increases pain in people with neuropathic pain following complete thoracic spinal cord injury. Pain 2008; 137: 237-44.

Hains B C, Saab C Y, Waxman S G. Changes in electrophysiological properties and sodium channel Na(v)1.3 expression in thalamic neurons after spinal cord injury. Brain 2005; 128: 2359-71.

Harris J A. Cortical origin of pathological pain. Lancet 1999; 354: 1464-66.

Hotz-Boendermaker S, Funk M, Summers P, Brugger P, Hepp-Reymond M C, Curt A, et al. Preservation of motor programs in paraplegics as demonstrated by attempted and imagined foot movements. Neuroimage 2008; 39: 383-94.

Knerlich-Lukoschus F, Juraschek M, Blomer U, Lucius R, Mehdorn H M, Held-Feindt J. Force-dependent development of neuropathic central pain and time-related CCL2/CCR2 expression after graded spinal cord contusion injuries of the rat. J Neurotrauma 2008; 25: 427-48.

Kokotilo K, Eng J, Curt A. Reorganization and preservation of motor control of the brain in spinal cord injury: a systematic review. J Neurotrauma 2009; 26: 2113-26.

Kumru H, Soto 0, Casanova J, Valls-Sole J. Motor cortex excitability changes during imagery of simple reaction time. Exp Brain Res 2008; 189: 373-8.

Lang N, Siebner H R, Ward N S, Lee L, Nitsche M A, Paulus W, et al. How does transcranial DC stimulation of the primary motor cortex alter regional neuronal activity in the human brain? Eur J Neurosci 2005; 22: 495-504.

Lefaucheur J P. Transcranial magnetic stimulation in the management of pain. Suppl Clin Neurophysiol 2004; 57: 737-48.

Lefaucheur J P, Drouot X, Menard-Lefaucheur I, Zerah F, Bendib B, Cesaro B, et al. Neurogenic pain relief by repetitive transcranial magnetic cortical stimulation depends on the origin and the site of pain. J Neurol Neurosurg Psychiatry 2004; 75: 612-16.

Lotze M, Flor H, Grodd W, Larbig W, Birbaumer N. Phantom movements and pain. An fMRI study in upper limb amputees. Brain 2001; 124: 2268-77.

Lotze M, Laubis-Herrmann U, Topka H. Combination of TMS and fMRI reveals a specific pattern of reorganisation in M1 in patients alter complete spinal cord injury. Restorative Neurol Neurosci 2006; 24: 97-107.

MacIver K, Lloyd D M, Kelly S, Roberts N, Nurmikko T. Phantom limb pain, cortical reorganization and the therapeutic effect of mental imagery. Brain 2008; 131: 2181-91.

Maeda F, Kleiner-Fisman G, Pascual-Leone A. Motor facilitation while observing hand actions: specificity of the effect and role of observer's orientation. J Neurophysiol 2002; 87: 1329-35.

Marino R J, Barros T, Biering-Sorensen F, Burns S P, Donovan W H, Graves D E, et al. 2002 ANSC. International standards for neurological classification of spinal cord injury. J Spinal Cord Med 2003; 26: 50-6.

Moore C I, Stern C E, Dunbar C, Kostyk S K, Gehi A, Corkin S. Referred phantom sensations and cortical reorganization after spinal cord injury in humans. Proc Natl Acad Sci USA 2000; 97: 14703-8.

Moseley G L. Using visual illusion to reduce at-level neuropathic pain in paraplegia. Pain 2007; 130: 294-8.

Nitsche M A, Liebetanz D, Antal A, Lang N, Tergau F, Paulus W. Modulation of cortical excitability by weak direct current stimulation-technical, safety and functional aspects. Suppl Clin Neurophysiol 2003; 56: 255-76.

Nitsche M A, Paulus W. Sustained excitability elevations induced by transcranial DC motor cortex stimulation in humans. Neurology 2001; 57: 1899-901.

Nitsche M A, Seeber A, Frommann K, Klein C C, Rochford C, Nitsche M S, et al. Modulating parameters of excitability during and after transcranial direct current stimulation of the human motor cortex. J Physiol 2005; 568: 291-303.

Pascual-Leone A, Amedi A, Fregni F, Merabet L B. The plastic human cortex. Annu Rev Neurosci 2005; 28: 377-401.

Pascual-Leone A, Grafman J, Hallett M. Modulation of cortical motor output maps during development of implicit and explicit knowledge. Science 1994; 263: 1287-9.

Peyron R, Garcia-Larrea L, Deiber M P, Cinotti L, Conyers P, Sindou M, et al. Electrical stimulation of precentral cortical area in the treatment of central pain: electrophysiological and PET study. Pain 1995; 62: 275-86.

Ramachandram V S, Hirstein W. The perception of phantom limbs. The D. O. Hebb lecture. Brain 1998; 121: 1603-30.

Ramachandran V S, Rogers-Ramachandran D. Synaesthesia in phantom limbs induced with mirrors. Proc Biol Sci 1996; 263: 377-86.

Redondo E, Asensio E, Navarro X, Verdu E. Thermal and mechanical algesimetry and electrophysiological wind-up after graded spinal cord injury in the rat: relationship to astroglial and microglial reactivity. Glia 2009; 57: S161.

Sakamoto M, Muraoka T, Mizuguchi N, Kanosue K. Combining observation and imagery of an action enhances human corticospinal excitability. Neurosci Res 2009; 65: 23-7.

Siddall P J, McClelland J M, Rutkowski S B, Cousins M J. A longitudinal study of the prevalence and characteristics of pain in the first 5 years following spinal cord injury. Pain 2003; 103: 249-57.

Soler M D, Kumru H, Vidal J, Pelayo R, Tormos J M, Fregni F, et al. Referred sensations and neuropathic pain following spinal cord injury. Pain 2010. Advance Access published on May 12, 2010; doi:10.1016/j.pain.2010.04.027.

Soler M D, Sauri-Ruiz J, Curcoll M L, Benito-Penalva J, Opiso-Salleras E, Vidal-Samso J. Characteristics of chronic neuropathic pain and their relationship with psychological well-being in spinal cord injury patients. Rev Neurol 2007; 44: 3-9.

Stinear C M, Byblow W D. Modulation of corticospinal excitability and intracortical inhibition during motor imagery is task-dependent. Exp Brain Res 2004; 157: 351-8.

Strafella A P, Vanderwerf Y, Sadikot A F. Transcranial magnetic stimulation of the human motor cortex influences the neuronal activity of subthalamic nucleus. Eur J Neurosci 2004; 20: 2245-9.

Wagner T, Valero-Cabre A, Pascual-Leone A. Noninvasive human brain stimulation. Annu Rev Biomed Eng 2007; 9: 527-65.

Waxman S G, Hains B C. Fire and phantoms after spinal cord injury: Na+ channels and central pain. Trends Neurosci 2006; 29: 207-15.

Widerström-Noga E G, Turk D C. Types and effectiveness of treatments used by people with chronic pain associated with spinal cord injuries: influence of pain and psychosocial characteristics. Spinal Cord 2003; 41: 600-9.

Woolf C J. Dissecting out mechanisms responsible for peripheral neuropathic pain: implications for diagnosis and therapy. Life Sci 2004; 74: 2605-10.

Wrigley P J, Press S R, Gustin S M, Macefield V G, Gandevia S C, Cousins M J, et al. Neuropathic pain and primary somatosensory cortex reorganization following spinal cord injury. Pain 2009; 141: 52-9.

Yezierski R P. Spinal cord injury: a model of central neuropathic pain. Neurosignals 2005; 14: 182-93. Yoon Y W, Dong H, Arends J J, Jacquin M F. Mechanical and cold allodynia in a rat spinal cord contusion model. Somatosens Mot Res 2004; 21: 25-31.

The invention claimed is:
1. A method for treating neuropathic pain, comprising:
providing, to a patient suffering from neuropathic pain, a visual illusion to correct a mismatch between motor commands and sensory feedback; and
applying a cranial stimulation to said patient during at least part of the duration of said visual illusion, so that pain intensity perception and anxiety are reduced, and these effects are long lasting, wherein said neuropathic pain comprises at least one of the next subtypes: continuous pain, paroxysmal pain, mechanical allodynia and dysaesthesia, as a consequence of any lesion at the central and/or peripheral nervous system.

2. A method as per claim 1, wherein said cranial stimulation is a transcranial stimulation.

3. A method as per claim 2, wherein said transcranial stimulation is a transcranial direct current stimulation.

4. A method as per claim 1, wherein said visual illusion is provided by showing the patient a video playing.

5. A method as per claim 4, wherein said video shows a body part of a person executing an action.

6. A method as per claim 5, further comprising providing a mirror, or any other device that can feed the patient with their own body image, in front of said patient, combined with a screen where said video is being displayed.

7. A method as per claim 1, further comprising starting the applying of said cranial stimulation a predetermined time before the providing of said visual illusion.

8. A method as per claim 1, further comprising starting the applying of said cranial stimulation at the same time than the start of said visual illusion.

9. A method as per claim 1, further comprising starting the applying of said cranial stimulation during the providing of said visual illusion.

10. A method as per claim 1, wherein said applying of said cranial stimulation relates to a first session, the method further comprising performing a further session of cranial stimulation after the providing of said visual illusion.

11. A method as per claim 1, further comprising applying said cranial stimulation to said patient by means of at least two stimulating non-invasive electrodes.

* * * * *